(12) United States Patent
Peleg et al.

(10) Patent No.: US 11,363,792 B2
(45) Date of Patent: Jun. 21, 2022

(54) SESAME CULTIVARS SUITABLE FOR MECHANICAL HARVEST WITH ENHANCED YIELD AND QUALITY

(71) Applicant: Yissum Research Development Company of the Hebrew University of Jerusalem Ltd., Jerusalem (IL)

(72) Inventors: Zvi Peleg, Moshav Herut (IL); Naama Teboul, Rishon Le-Zion (IL); Yaron Gadri, Moshav Moledet (IL)

(73) Assignee: YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 35 days.

(21) Appl. No.: 16/062,972

(22) PCT Filed: Dec. 15, 2016

(86) PCT No.: PCT/IL2016/051337
§ 371 (c)(1),
(2) Date: Jun. 15, 2018

(87) PCT Pub. No.: WO2017/103928
PCT Pub. Date: Jun. 22, 2017

(65) Prior Publication Data
US 2018/0359981 A1 Dec. 20, 2018

Related U.S. Application Data

(60) Provisional application No. 62/267,921, filed on Dec. 16, 2015.

(51) Int. Cl.
*A01H 5/10* (2018.01)
*A01H 6/66* (2018.01)
*C12N 15/82* (2006.01)

(52) U.S. Cl.
CPC .............. *A01H 6/66* (2018.05); *A01H 5/10* (2013.01); *C12N 15/8266* (2013.01)

(58) Field of Classification Search
None
See application file for complete search history.

(56) References Cited

U.S. PATENT DOCUMENTS

| | | | |
|---|---|---|---|
| 6,100,452 A | 8/2000 | Langham | |
| 6,781,031 B2 * | 8/2004 | Langham | A01H 6/66 435/430 |
| 8,080,707 B2 | 12/2011 | Langham | |
| 8,581,028 B2 | 11/2013 | Langham | |
| 8,664,472 B2 | 3/2014 | Langham | |
| 8,993,835 B2 | 3/2015 | Langham | |
| 10,577,623 B2 | 3/2020 | Gar | |
| 2003/0208798 A1 | 11/2003 | Langham | |
| 2009/0222940 A1 | 9/2009 | Langham | |
| 2011/0072533 A1 | 3/2011 | Langham | |
| 2011/0271360 A1 | 11/2011 | Langham | |
| 2015/0264879 A1 | 9/2015 | Langham | |

FOREIGN PATENT DOCUMENTS

| | | |
|---|---|---|
| IL | 200427 A | 3/2014 |
| WO | 00/13488 A1 | 3/2000 |

OTHER PUBLICATIONS

Wu et al. High-density genetic map construction and QTLs analysis of grain yield-related traits in sesame (*Sesamum indicum* L.) based on RAD-Seq technology. BMC Plant Biol. Oct. 10, 2014;14:274. (Year: 2014).*
Gu et al. High-resolution genetic mapping of bacterial blight resistance gene Xa10. Theor Appl Genet. Jan. 2008;116(2):155-63. Epub Oct. 9, 2007. (Year: 2008).*
Alonso et al. Moving forward in reverse: genetic technologies to enable genome-wide phenomic screens in *Arabidopsis*. Nat Rev Genet. Jul. 2006;7(7):524-36. Epub Jun. 6, 2006. Review. (Year: 2006).*
Qu et al. Generation and identification of *Arabidopsis* EMS mutants. Methods Mol Biol. 2014;1062:225-39. (Year: 2014).*
Bedigian, (2015) Systematics and evolution in *Sesamum* L.(Pedaliaceae), part 1: Evidence regarding the origin of sesame and its closest relatives. Webbia, 70(1), 1-42.
Uzun et al., (2003) Identification of a molecular marker linked to the closed capsule mutant trait in sesame using AFLP. Plant Breeding, 122(1), 95-97.
Uzun et al., (2004) Heterosis for agronomic traits in sesame hybrids of cultivars$^x$ closed capsule mutants. Acta Agriculturae Scandinavica, Section B—Soil & Plant Science, 54(2), 108-112.
Varshney et al., (2012) Can genomics boost productivity of orphan crops?. Nature biotechnology, 30(12), 1172-1176.
Wei et al., (2015) Genetic discovery for oil production and quality in sesame. Nature communications, 6, 8609, 1-10.
Zhang et al., (2013) Genome sequencing of the important oilseed crop *Sesamum indicum* L. Genome biology, 14(1), 401, 1-9.
Zhang et al., (2018) Identification of a SiCL1 gene controlling leaf curling and capsule indehiscence in sesame via cross-population association mapping and genomic variants screening BMC Plant Biol 18(1): 296; 12 pages.
Wang et al., (2014) Genome sequencing of the high oil crop sesame provides insight into oil biosynthesis. Genome Biol 15(2): R39; 13 pages.

* cited by examiner

*Primary Examiner* — Cynthia E Collins
(74) *Attorney, Agent, or Firm* — J.A. Lindeman & Co., PLLC (57) ABSTRACT

Provided are sesame plants having a mutation conferring closed capsules at maturity and means and methods for producing same. The plants of the present subject matter produce high yield of sesame seeds, the seeds having improved content of at least one of zinc, iron and calcium.

5 Claims, 8 Drawing Sheets

Specification includes a Sequence Listing.

SESAME CULTIVARS SUITABLE FOR MECHANICAL HARVEST WITH ENHANCED YIELD AND QUALITY

FIELD OF THE INVENTION

The present invention relates to sesame plants producing high yield of sesame seeds with improved nutritional quality and having indehiscent capsules at ripeness.

BACKGROUND OF THE INVENTION

Sesame (*Sesamum indicum* L., 2n=26), which belongs to the *Sesamum* genus of the Pedaliaceae family, is an important oil-crop worldwide. Sesame is one of the oldest crops in the world and has been under cultivation in Asia for over 5,500 years (Bedigian D. 2015. Webbia: Journal of Plant Taxonomy and Geography 70, 1-42). Sesame had spread into Africa, the Mediterranean and the Far East. Sesame is a tropical annual species grown for its oil and its nut flavored seeds. In the Middle East, a vast amount of sesame is consumed as sesame paste (tahini). In the Far East, sesame is widely used as cooking oil, and it is consumed for its medicinal properties. In the West, sesame seeds are primarily used for cooking and baking. The world production of sesame stands at about 5.4 (FAOstat, 2014). Nevertheless, sesame is in some respects an orphan crop-plant and it has been subjected to only limited research in modern genetics and breeding (Varshney R K et al., 2012. Nature Biotechnology 30, 1172-1176; Zhang H et al., 2013. Genome Biology 14, 401; Wei X et al., 2015. Nature Communications 6, 8609).

Sesame fruit is a capsule, normally pubescent, rectangular in section, and typically grooved with a short, triangular beak. The length of the fruit capsule varies from 2 to 8 cm, its width varies between 0.5 and 2 cm, and the number of loculi varies from four to 12. The sesame seeds are found within the fruit capsules. Upon maturity in nature, the capsules holding the sesame seeds begin to dry down, the capsules normally split open (dehiscent), and the seeds fall out. From ancient times through the present, the opening of the capsule has been the major factor in attempting successfully to collect the seed. For manual harvesting, it is important that the capsules are readily dehiscent, such that the seeds can be collected upon employment of minimal force, typically by shaking the stems holding the capsules. For mechanical harvesting, a balance should be reached between retaining seeds within the capsule during the harvest, e.g., by combine harvester, and releasing intact, commercially acceptable seeds from the capsules after harvest.

Throughout the ages, sesame seed and oil have been valued as a representative health food. The main constituents of sesame seeds are oil, protein, and carbohydrates. Among oil crops, sesame is one of the highest in oil content, ranging from 34 to 63%. Sesame oil consists of mainly four fatty acids (palmitic-C16:0, stearic-C18:0, oleic-C18:1 and linoleic-C18:2). The high levels of unsaturated (UFA) and polyunsaturated fatty acids (PUFAs) increase the quality of the oil for human consumption. Moreover, a high level of PUFAs in sesame oil is claimed to reduce blood cholesterol and high blood pressure, and play an important role in preventing atherosclerosis, heart diseases and cancers. The stability of sesame oil against oxidative degradation is attributed to the high levels of antioxidants such as sesamol, sesamin, sesamolin and sesaminol that are believed to promote the integrity of body tissues in the presence of oxidizing compounds.

Sesame seed contains about 20% protein that reaches 50% in the defatted seed. The major asset of sesame protein is its unique nutritional character, with high levels of the essential amino acids methionine and tryptophan. An in-vivo study on the nutritional quality of sesame protein demonstrated a significant decrease in total cholesterol and triglycerides upon consumption of the seeds.

The carbohydrate content of sesame seed is about 18-20%, most of which is present as dietary fibers. Sesame seed is rich in several mineral constituents, but their nutritive value has not been studied thoroughly.

Important nutrients iron, zinc and calcium, which are often deficient in modern human diets, are found in sesame seeds at relatively high concentrations.

While sesame seed is one of the oldest oilseed crops known, and the nutritional quality of its seeds is recognized, its growth is limited due a significant loss of yield during mechanical harvest of the seeds. Attempts at developing desirable sesame lines suitable for mechanical harvest have been made, addressing particularly the dehiscence characteristics of the capsules. U.S. Pat. Nos. 6,100,452; 8,080,707; 8664472; 8581028; and 8993835, all to Sesaco Corporation, disclose non-dehiscent sesame cultivars having various characteristics and methods of producing same.

There still an unmet need for, and it would be highly beneficial to have, sesame plants having indehiscent capsules that produce high yield of seeds with improved nutritional quality.

SUMMARY OF THE INVENTION

The present invention provides sesame plants that are exceptionally suitable for commercial production of high quality seeds. Particularly, the plants of the invention substantially retain all seeds within the plant capsule before harvest and shatter the seeds from the capsule only upon mechanical force, typically during mechanical harvest. The plants of the invention are elite cultivars producing high seed yields. Furthermore, the seeds produced by the plants of the invention are of high quality, comprising elevated amounts of micronutrients, particularly iron.

The present invention is based in part on the unexpected discovery of a linkage of the indehiscence phenotype to single nucleotide polymorphism (SNP) located on sesame linkage group (LG)-8. Furthermore, the present invention now shows that introgression of a minimal segment of LG-8 comprising the SNP or linked thereto into at least one cell of a plant confers to the plant not only a phenotype of indehiscent capsules but also an elevated seed concentration of calcium, iron and zinc.

According to one aspect, the present invention provides a sesame crop plant having a genetic element comprising a quantitative trait locus (QTL) conferring indehiscence phenotype to the plant, the QTL corresponds to a segment of wild type *Sesamum indicum* linkage group (LG)-8 spanning from position 5,162,951 to 7,447,238 or part thereof wherein the QTL nucleic acid sequence comprises at least one mutation compared to the wild type LG-8.

According to some embodiments, the QTL comprises at least one SNP. According to some embodiments, the SNP is selected from the group consisting of: T (Thymine) at position 5,176,856 on LG-8, T (Thymine) at position 5,207,071 on LG-8, A (Adenine) at position 5,164,512 on LG-8, G (Guanine) at position 5,107,812 on LG-8, A (Adenine) at position 5,448,993 on LG-8, and any combination thereof. Each possibility represents a separate embodiment of the invention. According to certain embodiments, the SNP is T (Thymine) at position 5,176,856 on LG-8.

According to some embodiments, the sesame crop plant is homozygous for a genetic element comprising said quantitative trait locus (QTL).

According to an additional aspect, the present invention provides a sesame crop plant having a genetic element comprising a quantitative trait locus (QTL) having a genetic linkage to at least one SNP, wherein said SNP is located within *Sesamum indicum* linkage group (LG)-8, said SNP is selected from the group consisting of: T (Thymine) at position 5,176,856 on LG-8, T (Thymine) at position 5,207,071 on LG-8, A (Adenine) at position 5,164,512 on LG-8, G (Guanine) at position 5,107,812 on LG-8, A (Adenine) at position 5,448,993 on LG-8, and any combination thereof, said QTL nucleic acid sequence comprises at least one mutation compared to the nucleic acids sequence of a wild type *Sesamum indicum* and wherein the QTL confers indehiscence phenotype to the plant.

According to yet additional aspect, the present invention provides a sesame crop plant having a genetic element comprising a quantitative trait locus (QTL) having a genetic linkage to position 5,176,856 on *Sesamum indicum* linkage group (LG)-8, said QTL nucleic acid sequence comprises at least one mutation compared to the nucleic acids sequence of a wild type *Sesamum indicum*, wherein the QTL confers indehiscence phenotype to the plant.

According to certain embodiments, the SNP is T (Thymine) at position 5,176,856 on LG-8.

According to certain embodiments, the plant comprising the QTL is characterized by closed capsules when said plant reaches full physiological maturity. According to certain embodiments, the mature plant is dry. According to some embodiments, the dry plant stands at the field. According to additional embodiments, the capsules are closed four weeks after the plant reaches full physiological maturity.

According to certain embodiments, the sesame plant comprises seeds having elevated content of at least one nutrient selected from the group consisting of zinc, iron, calcium and any combination thereof compared to the at least one nutrient content in seeds of a corresponding sesame crop plant lacking said QTL. Each possibility represents a separate embodiment of the present invention.

According to some embodiments, the sesame plant comprises seeds having at least 5%, 10%, 15%, 20%, 25%, or 30% more iron compared to seeds of a corresponding sesame crop plant lacking said QTL. Each possibility represents a separate embodiment of the invention.

According to some embodiments, the sesame plant comprises seeds having at least 5%, 10%, 15%, 20%, 25%, 30%, 35%, 40%, 45%, or 50% more zinc compared to seeds of a corresponding sesame crop plant lacking said QTL. Each possibility represents a separate embodiment of the invention.

According to certain embodiments, the QTL comprises a nucleic acid sequence at least 90% homologous to a nucleic acid sequence located within position 5,162,951 and position 7,447,238 of *Sesamum indicum* LG-8, said sequence comprises at least 80 nucleic acid residues. According to other embodiments, the QTL comprises a nucleic acid sequence at least 90% homologous to a nucleic acid sequence located within position 5,162,951 and position 5,515,472 of *Sesamum indicum* LG-8. According to some embodiments, said nucleic acid sequence has at least one SNP. According to certain exemplary embodiments, the SNP is selected rom the group consisting of: T (Thymine) at position 5,176,856 on LG-8, T (Thymine) at position 5,207,071 on LG-8, A (Adenine) at position 5,164,512 on LG-8, G (Guanine) at position 5,107,812 on LG-8, A (Adenine) at position 5,448,993 on LG-8, and any combination thereof. According to certain exemplary embodiments, the nucleic acid sequence comprises T (Thymine) at position 5,176,856 on LG-8.

According to certain exemplary embodiments, the QTL comprises the nucleic acid sequence set forth in SEQ ID NO:1. According to other exemplary embodiments, the QTL consists of the nucleic acid sequence set forth in SEQ ID NO:1.

According to certain embodiments of the invention, the genetic element consists of the QTL described hereinabove.

According to certain embodiments, the sesame plant is an inbred plant.

According to some embodiments, the sesame plant is a transgenic plant.

Advantageously, introgression of the QTL into a sesame plant according to the teachings of the present invention does not result in introgression of non-desired traits. Accordingly, the sesame plant of the invention is a cultivar suitable for commercial growth of sesame seeds, but it is not limited to a specific strain or variety.

According to certain embodiments, the sesame crop plant comprising the QTL produces higher seed yield compared to a corresponding sesame crop plant lacking the QTL. According to some exemplary embodiments, the sesame crop plant comprising the QTL produces at least 10% higher seed yield compared to a corresponding sesame crop plant lacking the QTL. According to some embodiments, the higher seed yield is obtained by mechanical harvesting. According to some embodiments, the mechanical harvesting is by a combine harvester. Other agronomical traits, including, but not limited to, growth rate, resistance to abiotic stresses and resistance to biotic stress are at least equivalent to corresponding sesame crop plant lacking the QTL.

It is to be explicitly understood that the sesame crop plants of the present invention are fertile, and seeds of said plants are explicitly encompassed within the scope of the present invention. Seeds as well as any other plant part that can be used for propagation, including isolated cells and tissue cultures are also encompassed within the scope of the present invention. It is to be understood that the plant produced from said seeds or other propagating material comprises the QTL. Plants grown from seeds homozygous for the QTL are indehiscent as described herein.

According to an additional aspect, the present invention provides a method for producing sesame plants having indehiscent capsules at maturity, the method comprising: introducing into at least one cell or part of a sesame plant having dehiscent capsules a genetic element comprising a QTL according to the invention. According to some embodiments, the QTL comprises at least one SNP. According to additional embodiments, the SNP is selected from the group consisting of: T (Thymine) at position 5,176,856 on LG-8, T (Thymine) at position 5,207,071 on LG-8, A (Adenine) at position 5,164,512 on LG-8, G (Guanine) at position 5,107,812 on LG-8, A (Adenine) at position 5,448,993 on LG-8, and any combination thereof. Each possibility represents a separate embodiment of the invention. According to certain embodiments, the SNP is T (Thymine) at position 5,176,856 of *Sesamum indicum* LG-8, thereby producing a sesame plant characterized by indehiscent capsules at maturity. According to additional embodiments, the QTL have a genetic linkage to a SNP as described hereinabove.

Any method as is known in the art can be used to introduce the genetic element comprising the QTL into a sesame plant.

According to certain exemplary embodiments, the genetic element is introduced by introgression.

According to other embodiments, the genetic element is introduced by transformation.

According to some embodiments, the present invention discloses hitherto unknown specific SNPs located within a QTL corresponding to sesame LG-8 or having a genetic linkage to said QTL that confer indehiscent phenotype to sesame plants naturally producing dehiscent capsules.

According to another aspect, the present invention provides an isolated polynucleotide comprising a nucleic acid sequence conferring indehiscent phenotype to a sesame plant, said nucleic acid sequence is at least 90% homologous to a nucleic acid sequence located within position 5,162,951 and position 7,447,238 of Sesamum indicum LG-8, said nucleic acid sequence comprises at least 80 nucleic acid residues. According to other embodiments, the isolated polynucleotide is at least 90% homologous to a nucleic acid sequence located within position 5,162,951 to position 5,515,472 of Sesamum indicum LG-8, nucleic acid sequence comprises at least 80 nucleic acid residues. According to some embodiments, said sequence has at least one SNP. According to some embodiments, the SNP is selected from the group consisting of: T (Thymine) at position 5,176,856 on LG-8, T (Thymine) at position 5,207,071 on LG-8, A (Adenine) at position 5,164,512 on LG-8, G (Guanine) at position 5,107,812 on LG-8, A (Adenine) at position 5,448,993 on LG-8, and any combination thereof. According to specific embodiments, the SNP is T (Thymine) at position 5,176,856 on LG-8. According to additional embodiments, the isolate polynucleotide comprises the nucleic acid sequence selected from the group consisting of: SEQ ID NO:1, SEQ ID NO:2, SEQ ID NO:3, SEQ ID NO:4, SEQ ID NO:5, and any combination thereof. Each possibility represents a separate embodiment of the invention. According to certain exemplary embodiments, the isolated polynucleotide comprises the nucleic acid sequence set forth in SEQ ID NO:1. According to certain additional exemplary embodiments, the isolated polynucleotide consists of the nucleic acid sequence set forth in SEQ ID NO:1.

According to yet another aspect, the present invention provides a method for identifying sesame plants having indehiscent phenotype, comprising detecting a QTL corresponding to LG8 of Sesamum indicum comprising an SNP selected from the group consisting of: T (Thymine) at position 5,176,856 on LG-8, T (Thymine) at position 5,207,071 on LG-8, A (Adenine) at position 5,164,512 on LG-8, G (Guanine) at position 5,107,812 on LG-8, A (Adenine) at position 5,448,993 on LG-8, and any combination thereof or having a genetic linkage to said SNP genomic localization in isolated genetic material obtained from the plant. Any method as is known in the art for isolating genetic material from at least a part of the sesame plant and for detecting the QTL in the genetic material can be used according to the teachings of the present invention.

According to certain exemplary embodiments, the QTL comprises the nucleic acid sequence set forth in SEQ ID NO:1. According to these embodiments, identifying sesame plants having indehiscent phenotype is performed by identifying SEQ ID NO:1 in the sesame plant. According to some embodiment, SEQ ID NO:1 is identified using a pair of amplification primers. According to certain exemplary embodiments, the pair of amplification primers comprises the nucleic acid sequence set forth in SEQ ID NO:6 (CGTCCTCGCTACATAATCCA) and SEQ ID NO:7 (TTG-GATCTACACGAGAGGTGA).

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 shows the visual difference between open capsules (FIG. 1A) and closed capsules (FIG. 1B).

FIG. 3 shows microscopy characterization of the dehiscence zone. Transverse sections in the middle of sesame capsule, 46 days after flowering.

FIG. 7 shows HRM graph of parental lines using HUSi002 (FIG. 7A), HUSi003 (FIG. 7B), HUSi004 (FIG. 7C) and HUSi005 (FIG. 7D) markers based on SNPs found on LG8. Indehiscent parent, S-91, and the dehiscent parent, S-297 are indicated.

DETAILED DESCRIPTION OF THE INVENTION

The present invention discloses for the first time a QTL corresponding to linkage group 8 of Sesamum indicum. The QTL comprises a genetic linkage to a single nucleotide polymorphism (SNP) T (tyrosine) instead of C (Cytosine), and is associated with the phenotype of closed (indehiscent) fully ripen capsules. The seeds within the indehiscent capsules comprise elevated seed concentration of zinc, iron and calcium. The present invention thus provides sesame plants comprising the QTL characterized by indehiscent capsules and methods of producing same. The present invention further provides isolated polynucleotides comprising the QTL or parts thereof useful in identifying indehiscent sesame plants. Advantageously, the sesame seeds remain in the sesame capsules even after the plant dries, which allows for a mechanical harvesting by a combine with a minimal loss of yield. Then, the combine can open the capsule and release the seeds as it is harvested. In addition, the sesame plant holds its seeds in capsules for four or more weeks after fully ripening, enabling flexibility in harvesting time.

Definitions

The term "plant" is used herein in its broadest sense. It also refers to a plurality of plant cells that are largely differentiated into a structure that is present at any stage of a plant's development. Such structures include, but are not limited to, a root, stem, shoot, leaf, flower, petal, fruit, etc. According to certain exemplary embodiments, the sesame plants of the present invention are hardy cultivars grown for commercial production of sesame seeds.

As used herein, the term "plant part" typically refers to a part of the sesame plant, including single cells and cell tissues such as plant cells that are intact in plants, cell clumps and tissue cultures from which sesame plants can be regenerated. Examples of plant parts include, but are not limited to, single cells and tissues from pollen, ovules, leaves, embryos, roots, root tips, anthers, flowers, fruits (capsules), stems, shoots, and seeds; as well as pollen, ovules, leaves, embryos, roots, root tips, anthers, flowers, fruits, stems, shoots, scions, rootstocks, seeds, protoplasts, calli, and the like.

The terms "dehiscence" or its adjective "dehiscent" as used herein with reference to a sesame plant or a sesame capsule (fruit) refer to a plant characterized by capsules or to the capsules per se that are visibly open when fully ripen (matured). The terms "indehiscence" or its adjective "indehiscent" as used herein with reference to a sesame plant or a sesame capsule (fruit) refer to a plant characterized by capsules or to the capsules per se that are visibly closed when fully ripen (matured). Without wishing to be bound by any specific theory or mechanism of action, the indehiscence phenotype is associated with increased number of cell layers between the median vascular bundle and the pericarp and the small numbers of cells with thin walls at this area. As a result, the tension force applied on the endocarp by the shrinking mesocarp upon dryness does not result in the rupture of the capsule wall.

The term "locus" (plural "loci") is defined herein as the position that a given gene occupies on a chromosome or a linkage group of a given species.

As used herein, the term "linkage group" refers to all of the genes or genetic traits that are located on the same chromosome. Within the linkage group, those loci that are close enough together will exhibit linkage in genetic crosses. Since the probability of crossover increases with the physical distance between genes on a chromosome, genes whose locations are far removed from each other within a linkage group may not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous to (the physical entity of) chromosome.

The term "QTL" (Quantitative Trait Loci) is used herein in its art-recognized meaning. The term QTL corresponding to sesame LG-8 that comprises or has a genetic linkage to an SNP selected from the group consisting of: T (Thymine) at position 5,176,856 on LG-8, T (Thymine) at position 5,207,071 on LG-8, A (Adenine) at position 5,164,512 on LG-8, G (Guanine) at position 5,107,812 on LG-8, A (Adenine) at position 5,448,993 on LG-8, and any combination thereof. The QTL according to the invention comprises at least one mutation. The term "QTL conferring indehiscent phenotype" refers to a region located on a particular linkage group of Sesamum indicum as described herein that may be associated with at least one gene that encodes for the indehiscent characteristics of the plant and/or for a regulatory region, i.e. a region of a chromosome that controls the expression of one or more genes involved in indehiscence. The phenotypic expression of that putative gene and/or regulatory region is typically closed capsules of a sesame plant standing in the field and ready for harvest. A QTL may for instance comprise one or more genes the products of which confer the indehiscence phenotype. Additionally or alternatively, a QTL may for instance comprise regulatory genes or sequences the products of which influence the expression of genes on other loci in the genome of the plant thereby conferring the indehiscence phenotype. The QTL of the present invention may be defined by indicating its genetic location in the genome of the respective *Sesamum indicum* accession using one or more markers. According to some embodiments, The QTL of the present invention is defined by the presence of "T" (Thymine) at position 5,176,856.

The term "homozygous" as is used herein means a genetic condition existing when identical alleles reside at corresponding loci on homologous chromosomes.

As used herein, the term "inbred" means a substantially homozygous individual plant or plant line.

The terms "introgression", "introgressed" and "introgressing" refer to the transmission of a desired allele(s) of a gene or trait locus from a genetic background of one species, variety or cultivar into the genome of another species, variety or cultivar. In one method, the desired allele(s) can be introgressed through a sexual cross between two parents, wherein one of the parents has the desired allele in its genome. The desired allele can include desired gene or genes, a marker locus, a QTL or the like.

The term "genetic element" is used in its broadest sense and includes a series of two or more nucleotides. The genetic element of the present invention comprises a mutated quantitative trait locus as described herein.

The terms "corresponding" or "corresponds" are used herein to describe the correlation between the QTL and a sequence such as *Sesamum indicum* linkage group (LG)-8, and refer to a position or region within a polynucleotide sequence that is identified by comparison to a reference sequence. The reference sequence is a wild-type form of the *Sesamum indicum* linkage group (LG)-8 sequence. In other words, the QTL sequence is identical to a sequence spanning from position 5,162,951 to 7,447,238 or part thereof of LG-8 except for at least one mutation. The mutation within the QTL may be, without limiting, a SNP, a deletion, or an insertion.

According to certain embodiments, the QTL is derived from the indehiscent plant of the present invention, *Sesamum indicum* S-91, seeds which have been deposited with NCIMB Ltd., Ferguson Building, Craibstone Estate, Bucksburn, Aberdeen, AB21 9YA Scotland on Nov. 1, 2021 and received deposit accession number NCIMB 43877.

According to certain embodiments, the QTL sequence comprises at least 100 contiguous nucleic acids identical to the wild type *Sesamum indicum* linkage group (LG)-8 except of the at least one mutation.

As used herein, the term "population" refers to a genetically heterogeneous collection of plants sharing a common genetic derivation.

According to one aspect, the present invention provides a sesame crop plant homozygous for a genetic element comprising a quantitative trait locus (QTL) comprising a single nucleotide polymorphism (SNP), wherein the QTL is derived from *Sesamum indicum* linkage group (LG)-8 and wherein the QTL confers indehiscence phenotype to the plant.

According to some embodiments, the SNPs are ad described above. According to certain embodiments, the SNP is T (Thymine) at position 5,176,856 on LG-8.

According to certain embodiments, the QTL comprises a nucleic acid sequence homologous to *Sesamum indicum* LG-8 sequence from position 5,162,951 to position 7,447,238. According to other embodiments, the QTL comprises a nucleic acid sequence homologous to sesame LG-8 sequence from position 5,162,951 to position 5,515,472. According to some embodiments, said nucleic acid sequence has at least one SNP. According to certain exemplary embodiments, the SNP is T (Thymine) at position 5,176,856 on LG-8.

The term "homologous" as used herein denotes a characteristic of a nucleic acid sequence, wherein a nucleic acid sequence has at least about 85 percent sequence identity as compared to a reference sequence, typically at least about 90 percent sequence identity, or at least about 95 percent sequence identity as compared to a reference sequence. The reference sequence may be a subset of a larger sequence, such as a portion of a chromosome, typically at least about 50 to 100 nucleotides long.

According to an additional aspect, the present invention provides a sesame crop plant having a genetic element comprising a quantitative trait locus (QTL), said QTL maps to a position between position 5,107,812 and position 5,448,993 on LG-8, said QTL nucleic acid sequence comprises at least one mutation and wherein said QTL confers indehiscence phenotype to the plant.

According to an additional aspect, the present invention provides a sesame crop plant comprising a genetic element comprising a quantitative trait locus (QTL), said QTL comprises genetic linkage to at least one SNP or its genomic localization, said SNP is selected from the group consisting of: T (Thymine) at position 5,176,856 on LG-8, T (Thymine) at position 5,207,071 on LG-8, A (Adenine) at position 5,164,512 on LG-8, G (Guanine) at position 5,107,812 on LG-8, A (Adenine) at position 5,448,993 on LG-8, and any combination thereof.

According to certain exemplary embodiments, the QTL comprises the nucleic acid sequence set forth in SEQ ID NO:2. According to these embodiments, identifying sesame plants having indehiscent phenotype is performed by identifying SEQ ID NO:2 in the sesame plant. According to some embodiment, SEQ ID NO:2 is identified using a pair of amplification primers. According to certain exemplary embodiments, the pair of amplification primers comprises the nucleic acid sequence set forth in SEQ ID NO:8 (CAGTAACCGCCCTTTGTGA) and SEQ ID NO:9 (CAAATGCGATTAAAAGTGAAACA).

According to certain exemplary embodiments, the QTL comprises the nucleic acid sequence set forth in SEQ ID NO:3. According to these embodiments, identifying sesame plants having indehiscent phenotype is performed by identifying SEQ ID NO:3 in the sesame plant. According to some embodiment, SEQ ID NO:3 is identified using a pair of amplification primers. According to certain exemplary embodiments, the pair of amplification primers comprises the nucleic acid sequence set forth in SEQ ID NO:10 (AGGGAGCGTTCTTCGGATA) and SEQ ID NO:11 (CGCCTCATTAGAGGGCAGT).

According to certain exemplary embodiments, the QTL comprises the nucleic acid sequence set forth in SEQ ID NO:4. According to these embodiments, identifying sesame plants having indehiscent phenotype is performed by identifying SEQ ID NO:4 in the sesame plant. According to some embodiment, SEQ ID NO:4 is identified using a pair of amplification primers. According to certain exemplary embodiments, the pair of amplification primers comprises the nucleic acid sequence set forth in SEQ ID NO:12 (GGTCCGAGAGAGCTGTTTTC) and SEQ ID NO:13 (ATCACAACTCGACCTGCTTG).

According to certain exemplary embodiments, the QTL comprises the nucleic acid sequence set forth in SEQ ID NO:5. According to these embodiments, identifying sesame plants having indehiscent phenotype is performed by identifying SEQ ID NO:5 in the sesame plant. According to some embodiment, SEQ ID NO:5 is identified using a pair of amplification primers. According to certain exemplary embodiments, the pair of amplification primers comprises the nucleic acid sequence set forth in SEQ ID NO:14 (GCAGCCAGGGTGGCTTAT) and SEQ ID NO:15 (GCACTAGCCGATATGTGCTTT).

The present invention discloses for the first time a genetic configuration resulting in indehiscence phenotype of a sesame plant. Plants comprising such configuration produce capsules that are kept closed when the plant reach maturity and dries; produce seeds with elevated amounts of significant nutrients including iron, zinc and/or calcium; and produce high seed yield.

The genetic unit "QTL" indicates a region on the genome that is directly related to a phenotypic quantifiable trait, the indehiscent phenotype according to the present invention. The QTL of the present invention has been first observed in $F_2$ population of a cross between a dehiscent line (S-297) and the mutated indehiscent line (S-91) produced by the inventors. The QTL was found to be associated with at least one marker, an SNP of T (Thymine) at position 5,176,856 of LG-8 instead of C (cytosine). The QTL of the invention may include one or more genes, which may or may not be related to the indehiscent phenotype.

As described in the Example section hereinbelow, an efficient High Resolution Melt (HRM) marker was developed based on the identified SNP detected on LG-8. Amplification of a QTL fragment comprising the SNP was performed using the primers having the nucleic acids sequences set forth in SEQ ID NO:2 (forward) and SEQ ID NO:3 (reverse). The resulted amplicon contained 84 nucleic acids. The mutated amplicon comprising the SNP consists of SEQ ID NO: 1. The marker was tested by HRM on the parental lines as well as on $F_1$ and $F_2$ progenies in order to test its efficiency (FIGS. 4-6) and was found to be highly efficient. The efficiency was also demonstrated with various other crosses (data not shown).

The present invention further provides a method for identifying sesame plants having indehiscent phenotype, comprising detecting a mutated QTL corresponding to LG-8 of *Sesamum indicum* comprising SNP of T (Thymine) at position 5,176,856 in an isolated genetic material obtained from the plant. It is to be explicitly understood that the SNP marker identified in the present invention is an example of markers suitable for use in marker assisted selection (MAS) procedures. Additional markers associated with the QTL conferring indehiscence phenotype, as such markers may exist, are also encompassed within the scope of the present invention.

The present invention further provides a method for producing sesame plant characterized by indehiscent capsules at maturity, the method comprises introducing into at least one cell or part thereof of a sesame plant characterized by dehiscent capsule a genetic element comprising a QTL derived from LG-8 of *Sesamum indicum* plant characterized by indehiscent capsule, the QTL comprises an SNP of T (Thymine) at position 5,176,856, thereby producing a sesame plant characterized by indehiscent capsules at maturity.

Introducing the genetic element comprising the QTL conferring indehiscent phenotype according to the teachings of the present invention can be performed by any method as is known to a person skilled in the art. It is to be explicitly understood that in the sesame plant produced, the segment comprising the QTL is not in its natural background. As used herein, the term "natural genetic background" indicates the original genetic background of a QTL. Such a background is the genome of the mutated *Sesamum indicum* produced as described herein. Accordingly, *S. indicum* line S-91 represents the natural genetic background of the QTL of the invention. A method involving the transfer of DNA comprising the QTL from linkage group 8 of *S. indicum* to the same or different position on the corresponding linkage group of another *S. indicum* lines will result in that the QTL or part thereof not being in its natural genetic background.

Alternatively, nucleic acid (preferably DNA) sequence comprising the QTL of the present invention or any part thereof that can confer indehiscence phenotype as disclosed herein may be used for the production of indehiscent sesame plants. According to certain embodiments, the QTL is introduced into dehiscent sesame plant, typically a cultivar suitable for commercial growth. According to the teachings of the present invention, said nucleic acid sequence is derived from mutated *S. indicum* donor plant.

The QTL conferring indehiscence phenotype can be isolated from the donor plant by using any method as is known in the art.

The QTL sequence may be transferred to a recipient sesame plant by any method as is known to a person skilled in the art. According to certain embodiments, the QTL can be introduced by crossing the donor with a recipient dehiscent sesame plant (i.e. by introgression). Alternatively, isolated nucleic acid sequence comprising the QTL can be introduced by transformation as described hereinbelow. Transformation is optionally followed by selection of offspring plants comprising the QTL and exhibiting indehiscence phenotype.

Transforming plants with isolated nucleic acid sequence generally involves the construction of an expression vector that will function in plant cells. According to the teachings of the present invention, such a vector comprises the QTL of the invention or part thereof. Typically, the vector comprises the QTL under control of or operatively linked to a regulatory element. According to certain embodiments, the regulatory element is selected from the group consisting of a promoter, enhancer, a translation termination sequence, and any combinations thereof. The vector(s) may be in the form of a plasmid, and can be used, alone or in combination with other plasmids, in a method for producing transgenic indehiscent sesame plants.

Expression vectors can include at least one marker (reporter) gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the markers gene). Many commonly used selectable marker genes for plant transformation are known in the art, and include, for example, genes that code for enzymes that metabolically detoxify a selective chemical agent which may be an antibiotic or an herbicide, or genes that encode an altered target which is insensitive to the inhibitor. Several positive selection methods are known in the art, such as mannose selection. Alternatively, the presence of the QTL in the transformed plant is identified using the marker of the present invention.

Methods for transforming a plant cell with nucleic acids sequences according to the present invention are known in the art. As used herein the term "transformation" or "transforming" describes a process by which a foreign nucleic acid sequence, such as a vector, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait. According to typical embodiments the nucleic acid sequence of the present invention is stably transformed into a plant cell.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Phenotypic Measurements

Phenotyping the trait for capsule dehiscence was conducted at the end of plants growth, when the plant had dried and reached full physiological maturity. Each plant from the $F_2$ population and both of the parental lines were marked as "open" or "closed" capsule.

Micronutrients Analysis

Sesame seeds were grind in a coffee grinder for 5-10 sec each. A batch of each sample (about 250 mg of dry material) was digested in 8 ml of 65% $HNO_3$ and 2 ml of 30% $H_2O_2$. Internal standard Yttrium (Y) was used to control digestion process quality and possible matrix effects. Digestion was carried out in Teflon vessels using a "Milestone Ethos 1" microwave-digestion-system at high temperature and pressure. During 20 min the temperature inside the vessel was increased linearly to 180° C. using 900W energy, then the temperature was maintained during next 15 min at 180° C. Vessels were cooled down and the volume was made up to 25 ml with deionized water. Micronutrient concentration was measured in the clear solutions using a radial ICP-OES model 'ARCOS' from Spectro GMBH, Germany, equipped with cross-flow nebulizer and Scott spray chamber. Measurements were calibrated with standards for ICP from Merck. Element concentrations that exceed the linear dynamic range were diluted and reanalysed. Dilution was made using calibrated pipettes. The continuing calibration verification standard was measured at least every 10 samples to check the instrument stability.

Example 1

Development of an Indehiscent Sesame Line

Sesame plants characterized by closed capsules at maturity were developed by mutagenesis of sesame seeds. Seeds from a collection of dehiscent sesame plants were used. Follow calibration, the sesame seeds were soaked in $ddH_2O$ for 4 hours, and then treated with 1% of Ethyl methanesulfonate (EMS) for 24 hours at room temperature (24° C.). After treatment, the seeds were washed for 4 hours under running water. The washed seeds were sown in planting trays with clay and grown until four leaves stage (14-20 days) and then transplanted into the field ($M_0$ plants).

Figure 1A:
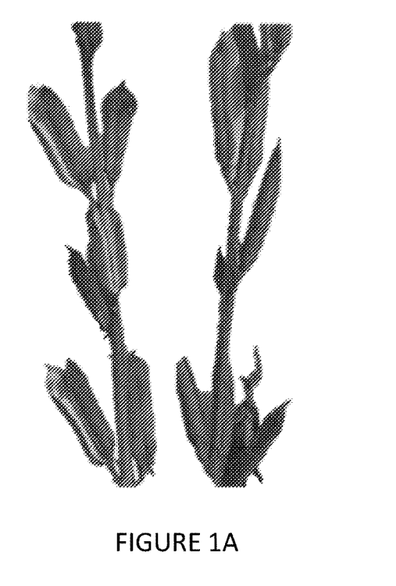
Figure 1B:
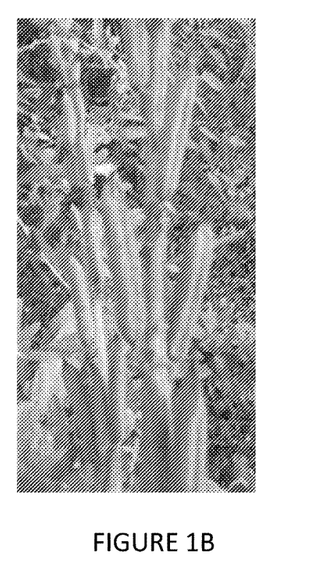

The seeds produced by the $M_0$ plants ($M_1$ generation) were collected and after cleaning they were sown in the field to get $M_2$ seeds. $M_2$ seeds were sown in the field and the resulting plants were characterized for indehiscence capsule phenotype. Characterization was made by visible differentiation between open capsules (FIG. 1A) and closed capsules (FIG. 1B). About 120,000 M2 plants were screened in the field.

The obtained $M_2$ plant was backcrossed with the parental line for three generations to get homozygote line. The homozygous line, designated S-91, was used for the production of the mapping population.

Example 2

Production of Mapping Population

Figure 2:
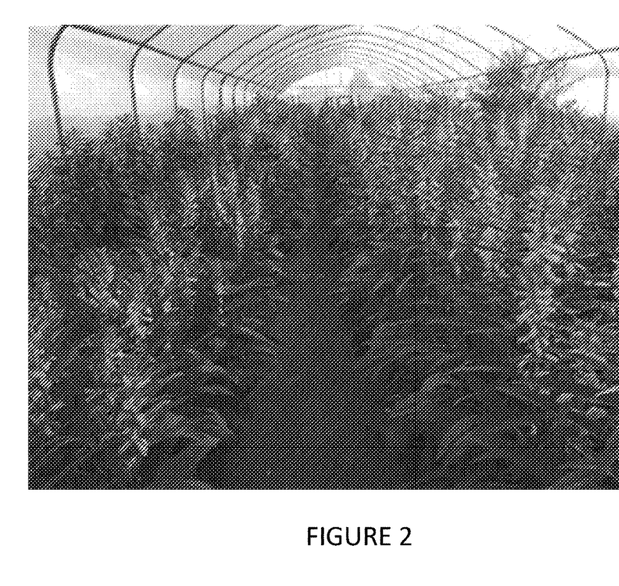
FIG. 2 is a representative picture of $F_2$ population grown in a net-house.

An indehiscent line (S-91) was crossed with dehiscent line (S-297) and the $F_1$ progeny was selfed to produce an $F_2$ mapping population of 148 lines. This population, alongside with the two parental lines was grown in insect proof net-house (FIG. 2). The plants were phenotyped for morphological, physiological and yield components and for quality traits.

Figure 3A:
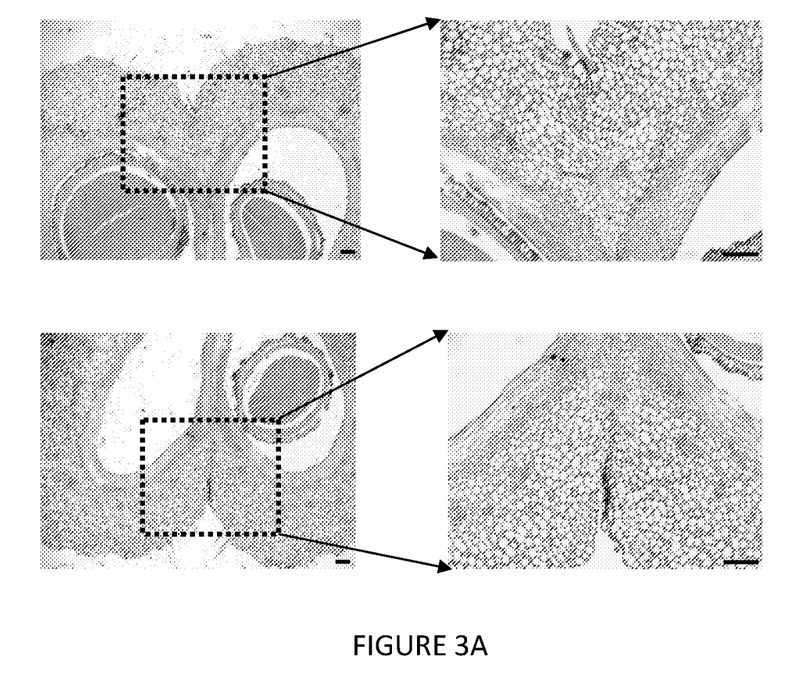
FIG. 3A: two representative images of indehiscent parental line, S-91 (left images; right—enlarged images as indicated).
Figure 3B:
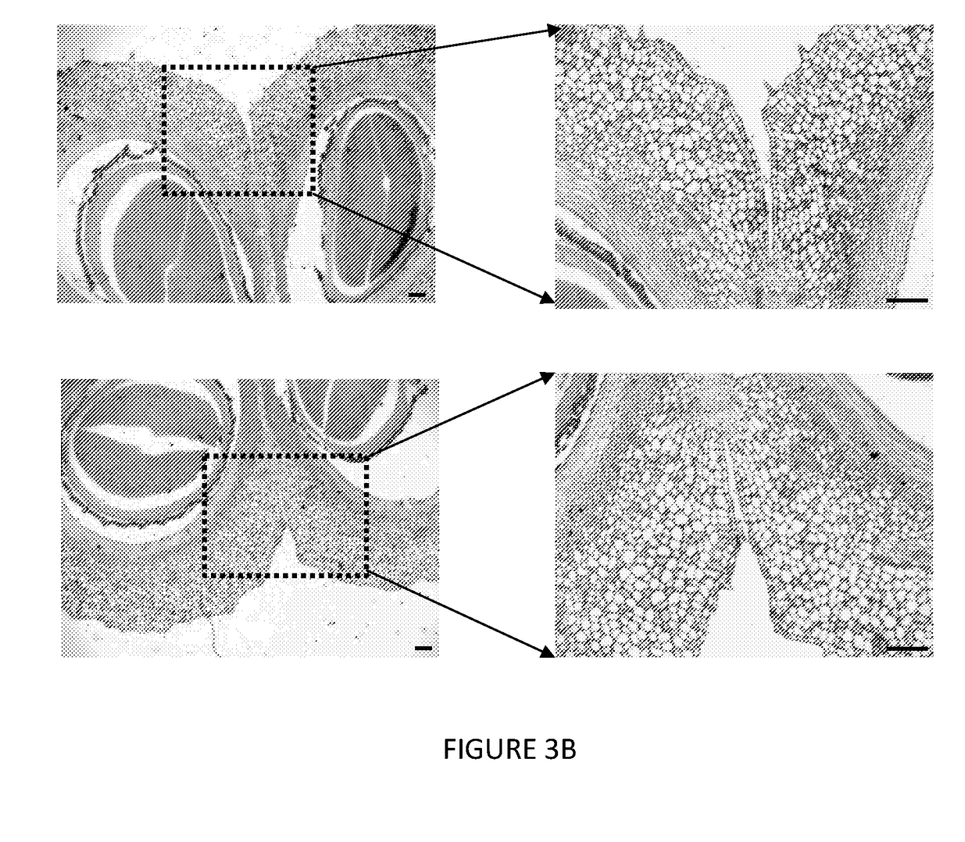
FIG. 3B: two representative images of the dehiscent parental line, S-297 (left images; right—enlarged images as indicated).
Figure 3C:
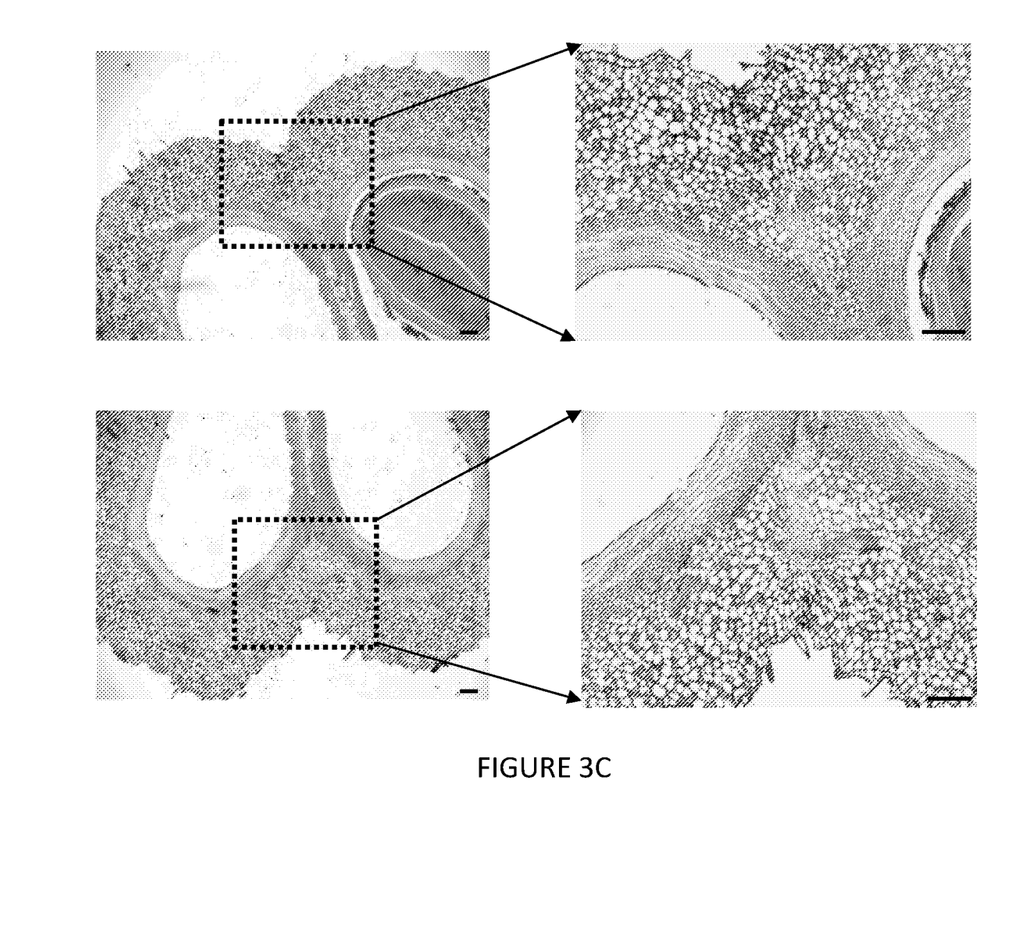
FIG. 3C: two representative images of $F_2$ indehiscent offspring from a cross between S-91×S-297 (left images; right—enlarged images as indicated). Bar=200 µm.

Microscopy characterization of the dehiscence zone was performed for the indehiscent line (S-91), the dehiscent line (S-297) and for a representative $F_2$ indehiscent line. FIG. 3 shows transverse sections in the middle of sesame capsule, 46 days after flowering. The clear rupture of the capsule of the dehiscent capsule (FIG. 3B) is missing from the indehiscent capsules (FIGS. 3A and 3C).

Example 3

QTL Analysis

Figure 4:
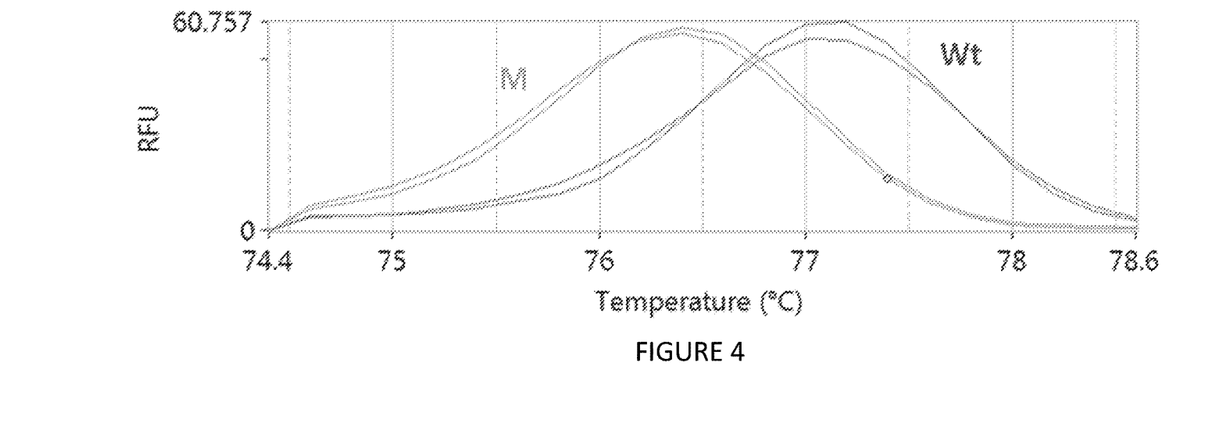
FIG. 4 shows High Resolution Melt (HRM) graph of parental lines using HUSi001 marker based on the SNP found on LG8. Indehiscent parent, S-91, and the dehiscent parent, S-297, marked as "M" and "Wt" respectively (Two replicates each).
Figure 5:
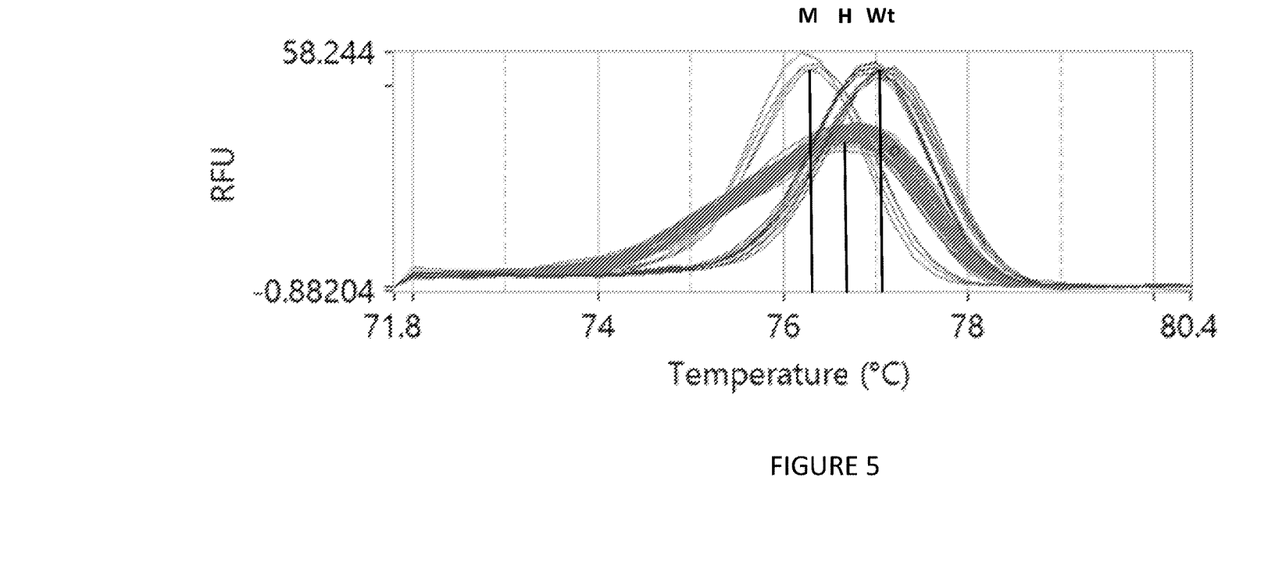
FIG. 5 shows HRM graph of dehiscent S-297 and S-65 (WT), indehiscent S-91 (M) lines and several backcross lines (H). The backcross ($BC_1F_1$) derived from a cross between the indehiscent $F_2$ offspring and his dehiscent parent.
Figure 6:
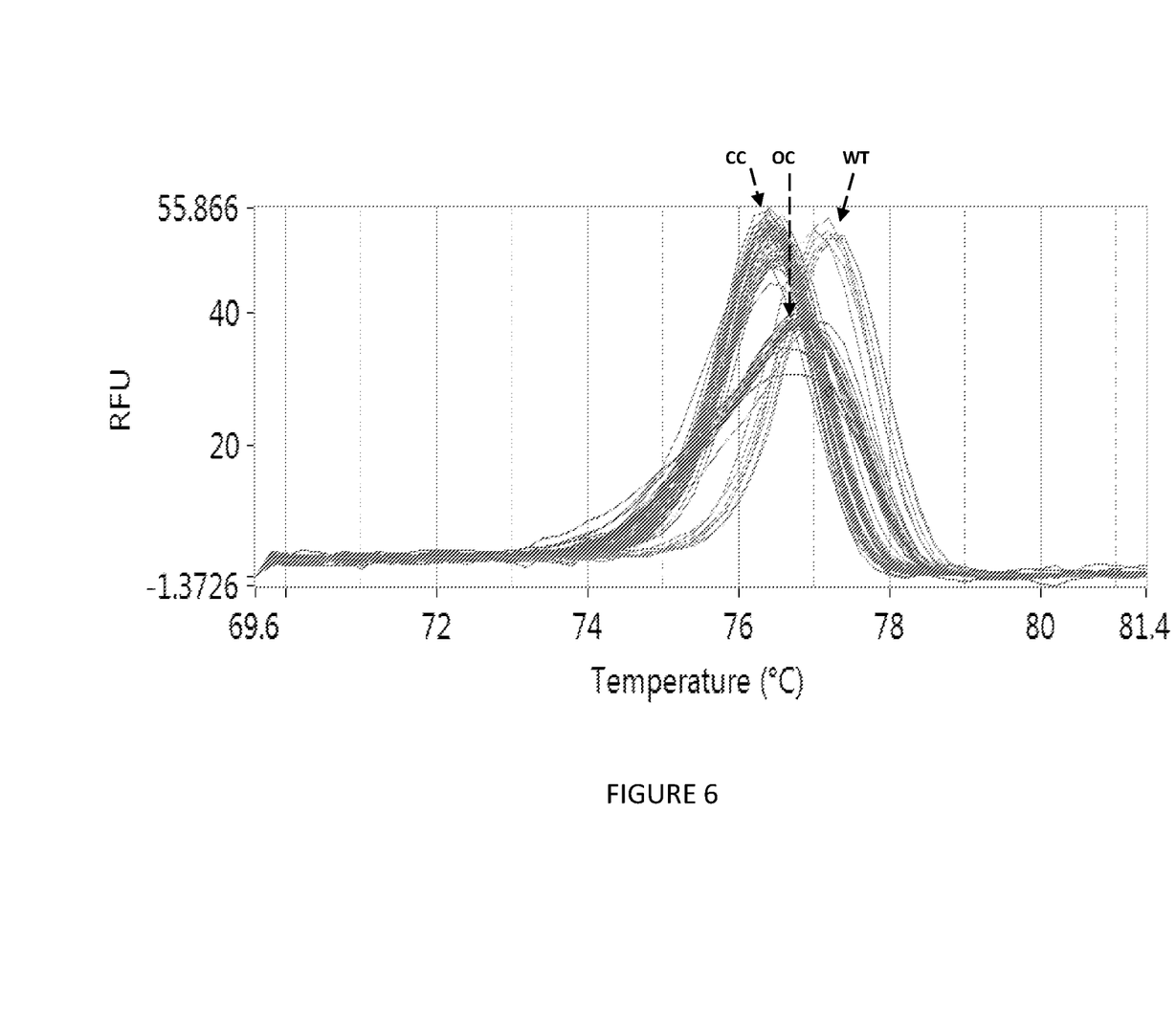
FIG. 6 shows HRM graph of several $F_2$ lines sharing a mutual parent (S-91). Lines with indehiscence capsule phenotype (CC) and lines with WT (dehiscence) capsule phenotype (OC).
Figure 7A:
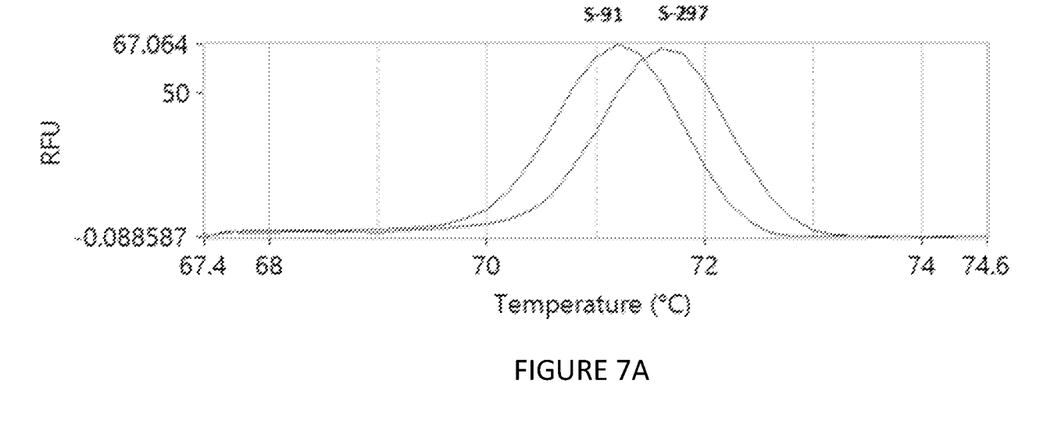
Figure 7B:
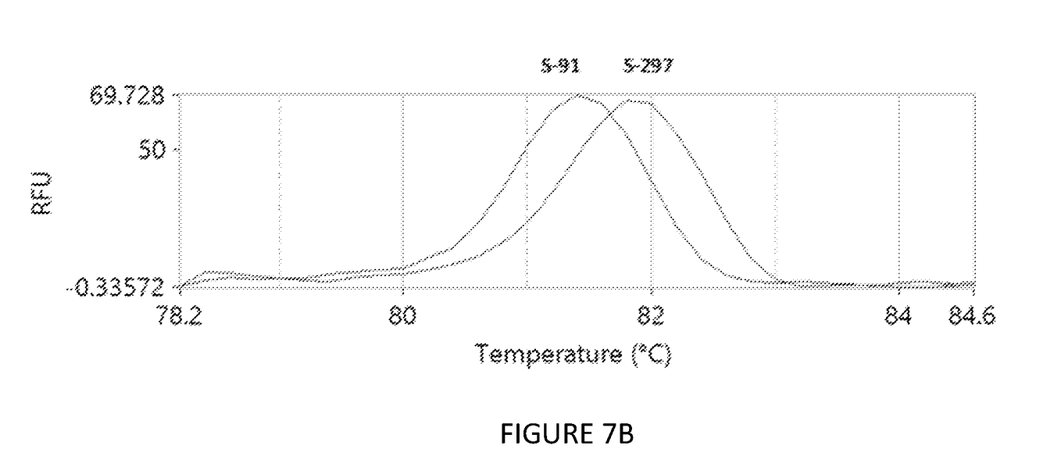
Figure 7C:
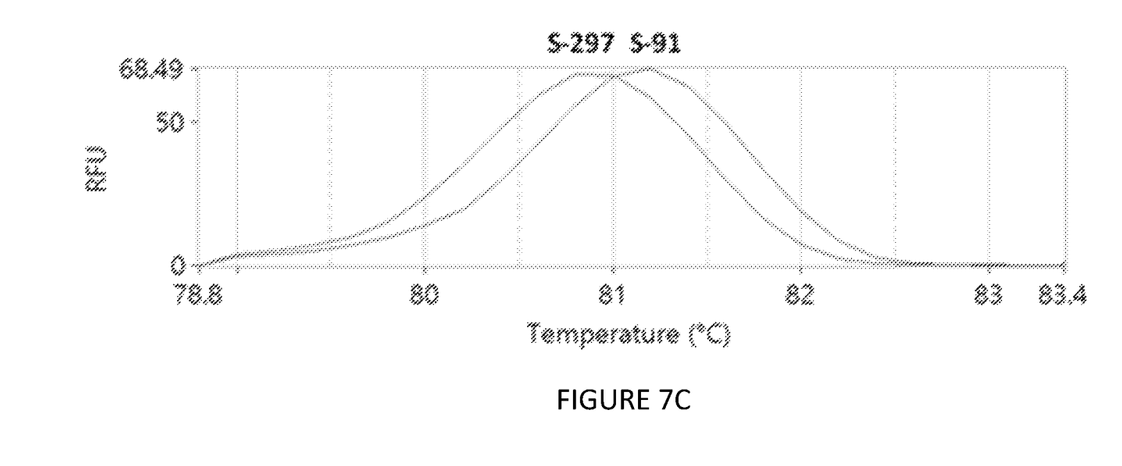
Figure 7D:
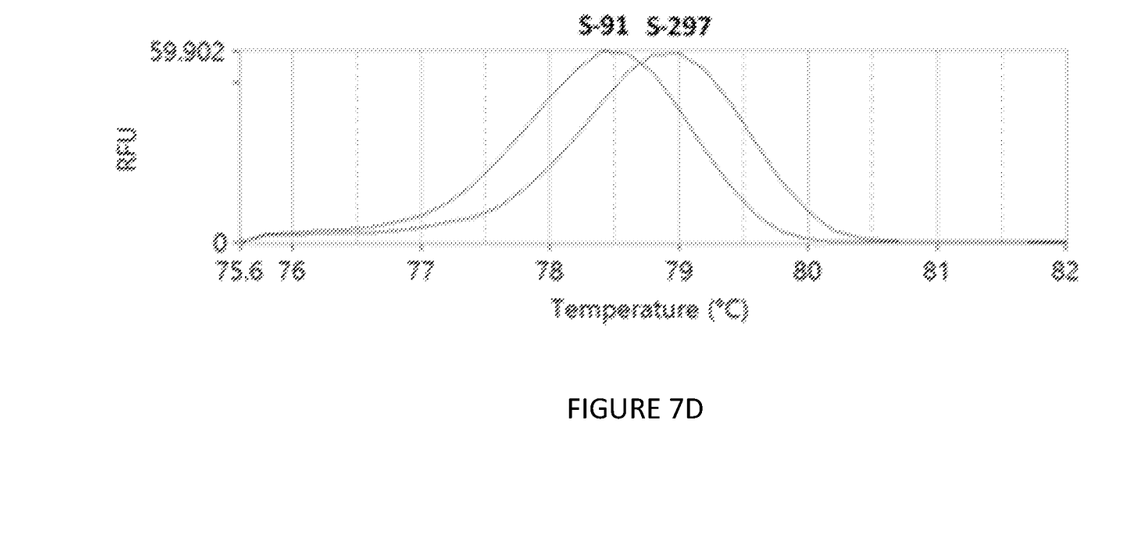

The mapping population was genotyped using genotype-by-sequencing (GBS), performed by Energin R Technologies 2009 LTD. (NRGene, http://nrgene.com). A high-density genetic map was constructed (including about 20,000 SNPs). QTLs analysis was conducted on the F2 population and revealed the genetic location of the indehiscence and seed nutrient traits (Table 1). An SNP at position 5,176,856 was identified, with the dehiscent plants comprising "C" (Cytosine) at this location and the indehiscent plant comprising "T" (Thymine) at this location. Based on the identified SNP detected on LG-8, an efficient High Resolution Melt (HRM) marker was developed (FIG. 4). The amplification primers included a left primer having the nucleic acid sequence set forth in SEQ ID NO:6 (CGTCCTCGCTACAT-AATCCA) and a right primer having the nucleic acid sequence set forth in SEQ ID NO:7 (TTGGATCTA-CACGAGAGGTGA). The amplification product comprises 84 nucleic acids (SEQ ID NO:1): CGTCCTCGCTACAT-AATCCAACTGTACTGGATAAAGCTTATGATGTT-CATGT TTGTGACACAATCACCTCTCGTGTAGATC-CAA (the SNP is marked within a rectangle). This marker was tested on the parental lines as well as $F_1$ and $F_2$ progenies in order to test its efficiency (FIGS. 4-6).

TABLE 1

Major QTLs detected on LG-8 for the indehiscence trait (qualitative: open vs. close) and seed nutrient (iron, zinc and calcium) concentration.

| Trait name | LG starts | LG ends | Peak start | Peak ends | P-value | $R^2$ | LOD score |
|---|---|---|---|---|---|---|---|
| Capsule dehiscence | 5,162,951 | 5,515,472 | 5,162,951 | 5,515,472 | 0 | 1 | Inf. |
| Seed Calcium | 4,497,023 | 7,823,496 | 5,162,951 | 6,306,717 | 2.07E−08 | 0.214 | 7.84 |
| Seed Iron | 4,374,000 | 9,570,814 | 5,162,951 | 7,447,238 | 1.65E−08 | 0.216 | 7.94 |
| Seed Zinc | 4,374,000 | 7,667,265 | 5,162,951 | 7,125,811 | 3.04E−20 | 0.457 | 19.92 |

Example 4

Seed Nutrient Concentration

Micronutrient analysis was performed in seeds of the indehiscent line developed in the present invention (S-91) and of the dehiscent line (S-297) as described in "Material and Methods" hereinabove. Table 2 present elevated amounts of all nutrients examined in seeds produced by indehiscent plants comprising the SNP marker. A significant increase in the amount of zinc (55%), iron (30%) and calcium (12%) was found (Table 2). This result is of high significance, as food sources of zinc and iron are highly desired.

TABLE 2

Concentration of calcium, iron and zinc in seeds of S-91 and S-297.

| Genotype | Seed nutrient concentrations (mg/kg) | | |
|---|---|---|---|
| | Calcium | Iron | Zinc |
| S-91 | 12193.324* | 108.561* | 92.912* |
| S-297 | 10386.674 | 82.978 | 60.083 |

*Indicate significant differences between the two sesame genotypes (student-t test) at $P \leq 0.05$.

Example 5

Plant Material Tested With HUSi001 HRM Marker

In order to test HUSi001 marker efficiency in differentiating between dehiscence and non-dehiscence capsules under different genetic backgrounds, non-dehiscent line S-91 were crossed with 28 dehiscent lines from the Hebrew University collection (S-4, S-8, S-10, S-34, S-37, S-43, S-46, S-47, S-53, S-59, S-64, S-65, S-67, S-79, S-80, S-92, S-100, S-110, S-274, S-278, S-289, S-301, S-308 S-313, S-315, S-316, S-326, S-1038). The F1 hybrids were grown in a net-house and seeds were collected from each F1 plants. F$_2$ seeds were sown in the field (10 seeds from each cross) and characterized for capsule morphology. Young leaves from 5-8 plants of each cross were collected (108 samples in total) and used for DNA extraction. All samples were analyzed in HRM with HUSi001 marker and resulted in 100% ability of the HUSi001 to differentiate between dehiscence and non-dehiscence capsule.

Additionally, HUSi001 marker was used for backcross screening. Two indehiscent F$_2$ were chosen from 3 different families: plants #55 and #149 from S-91×S-297, #53 and #166 from S-91×S-65, and #57 and #92 from S-8×S-91. The plants were correspondingly backcrossed with the dehiscent parent (i.e. S-297, S-65 or S-8) in order to create near isogenic lines (NILs). Each backcross generation was scanned with HUSi001 marker to ensure successful fertilization; 66 BC$_1$F$_1$, 23 BC$_2$F$_1$, 78 BC$_2$F$_2$, and 174 BC$_3$F$_1$ plants were scanned.

Example 6

Plant Material Tested With Different Markers

HUSi002, HUSi003, HUSi004, and HUSi005 Markers were found to be efficient in differentiating between dehiscence and non-dehiscence capsules. A representative High Resolution Melt (HRM) graphs of indehiscent line (S-91) and dehiscent line (S-297) are shown in FIGS. 7A-7D. The amplification primers were SEQ ID NOs: 8 and 9 for HUSi002; SEQ ID NOs: 10 and 11 for HUSi003; SEQ ID NOs: 12 and 13 for HUSi004; and SEQ ID NOs: 12 and 13 for HUSi005.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A sesame crop plant or a part thereof having a genetic element comprising a quantitative trait locus (QTL) conferring an indehiscence phenotype to the plant, the QTL comprising a segment of linkage group (LG)-8 spanning from position 5,162,951 to 7,447,238, wherein the QTL is present in the genome of a Sesamum indicum S-91 plant, seeds of which have been deposited with NCIMB Ltd. as the International Depositary Authority under Accession No. NCIMB 43877, wherein the QTL comprises the nucleic acid sequence set forth in SEQ ID NO:1, and wherein the sesame crop plant is characterized by closed capsules when said plant reaches full maturity and by seeds having elevated content of zinc, iron, and calcium compared to seeds of a corresponding sesame crop plant lacking the QTL.

2. A seed of the sesame crop plant of claim 1, wherein said seed comprises the QTL.

3. A method for producing sesame plants having indehiscent capsules at maturity, the method comprising: introducing into at least one cell or part of a sesame plant characterized by dehiscent capsules a genetic element comprising a quantitative trait locus (QTL) comprising a segment of linkage group (LG)-8 spanning from position 5,162,951 to 7,447,238, wherein the QTL is present in the genome of a Sesamum indicum S-91 plant, seeds of which have been deposited with NCIMB Ltd. as the International Depositary Authority under Accession No. NCIMB 43877, wherein said QTL comprises the nucleic acid sequence set forth in SEQ ID NO:1, thereby producing a sesame plant characterized by closed capsules at maturity and by seeds having elevated content of zinc, iron, and calcium compared to seeds of a corresponding sesame crop plant lacking the QTL.

4. The method of claim 3, wherein the genetic element is introduced by introgression.

5. A plant produced by the method of claim 3, wherein said plant comprises the QTL.

\* \* \* \* \*

```
                        SEQUENCE LISTING

<160> NUMBER OF SEQ ID NOS: 15

<210> SEQ ID NO 1
    <211> LENGTH: 84
    <212> TYPE: DNA
    <213> ORGANISM: Sesamum indicum

<400> SEQUENCE: 1
cgtcctcgct acataatcca actgtactgg ataaagctta tgatgttcat gtttgtgaca      60
caatcacctc tcgtgtagat ccaa                                             84

<210> SEQ ID NO 2
    <211> LENGTH: 99
    <212> TYPE: DNA
    <213> ORGANISM: Sesamum indicum

<400> SEQUENCE: 2
cagtaaccgc cctttgtgag taaaaatgag ttttctttag agaaaagata atattttta       60 tctcataagt taagcttgtt tcacttttaa tcgcatttg                             99

<210> SEQ ID NO 3
    <211> LENGTH: 83
    <212> TYPE: DNA
    <213> ORGANISM: Sesamum indicum

<400> SEQUENCE: 3
agggagcgtt cttcggataa ctgccactca cacgtccgtt agcctcttct ccacatgctt      60
ggtaactgcc ctctaatgag gcg                                              83

<210> SEQ ID NO 4
    <211> LENGTH: 120
    <212> TYPE: DNA
    <213> ORGANISM: Sesamum indicum

<400> SEQUENCE: 4
```

-continued

```
gggattgttg tttagccaac cacccccagca acatttccca gatctactcc ttggttctgg      60
cgaaaacagc tctctcggac cgacctacta cagatgtaag ccccaagtat tgtcaagct      120
```

<210> SEQ ID NO 5
<211> LENGTH: 120
<212> TYPE: DNA
<213> ORGANISM: Sesamum indicum

<400> SEQUENCE: 5

```
agcttttaca taagtcgccc tagttagtgc ttacatttgt gtaagccgca ctagccgata       60
tgtgctttta cataagtcgc cctaggtgat gaatacattt gtaagtcact atagctagcg      120
```

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6

```
cgtcctcgct acataatcca                                                   20
```

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7

```
ttggatctac acgagaggtg a                                                 21
```

<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8

```
cagtaaccgc cctttgtga                                                    19
```

<210> SEQ ID NO 9
<211> LENGTH: 23
<212> TYPE: DNA
<213> ORGANISM: Artificial sequence
<220> FEATURE:
<223> OTHER INFORMATION: Primer

<400> SEQUENCE: 9

```
caaatgcgat taaaagtgaa aca                                               23
```

<210> SEQ ID NO 10
<211> LENGTH: 19
<212> TYPE: DNA
<213> ORGANISM: Artificial sequence
<220> FEATURE:
<223> OTHER INFORMATION: Primer

<400> SEQUENCE: 10

```
agggagcgtt cttcggata                                                    19
```

<210> SEQ ID NO 11
<211> LENGTH: 19

```
-continued

<212> TYPE: DNA
<213> ORGANISM: Artificial sequence
<220> FEATURE:
<223> OTHER INFORMATION: Primer

<400> SEQUENCE: 11
cgcctcatta gagggcagt                                                  19

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
ggtccgagag agctgttttc                                                 20

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
atcacaactc gacctgcttg                                                 20

<210> SEQ ID NO 14
<211> LENGTH: 18
<212> TYPE: DNA
<213> ORGANISM: Artificial sequence
<220> FEATURE:
<223> OTHER INFORMATION: Primer

<400> SEQUENCE: 14
gcagccaggg tggcttat                                                   18

<210> SEQ ID NO 15
<211> LENGTH: 21
<212> TYPE: DNA
<213> ORGANISM: Artificial sequence
<220> FEATURE:
<223> OTHER INFORMATION: Primer

<400> SEQUENCE: 15
gcactagccg atatgtgctt t                                               21
```